United States Patent [19]

Berg

[11] Patent Number: 5,198,077
[45] Date of Patent: * Mar. 30, 1993

[54] RECOVERY OF GLYCERINE FROM MANNITOL, LACTOSE OR LACTITOL BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[*] Notice: The portion of the term of this patent subsequent to Mar. 2, 2010 has been disclaimed.

[21] Appl. No.: 794,877

[22] Filed: Nov. 19, 1991

[51] Int. Cl.$^5$ .................. B01D 3/36; C07C 29/82
[52] U.S. Cl. ........................... 203/60; 203/69; 568/869
[58] Field of Search ............... 203/69, 60; 568/869

[56] References Cited

U.S. PATENT DOCUMENTS

| | | | |
|---|---|---|---|
| 2,004,135 | 6/1935 | Rothrock | 568/869 |
| 2,154,930 | 4/1939 | Evans | 568/869 |
| 4,560,812 | 12/1985 | Blytas | 568/869 |
| 4,975,158 | 12/1990 | Berg | 203/68 |
| 4,980,033 | 12/1990 | Berg | 203/69 |

FOREIGN PATENT DOCUMENTS 56-158712 12/1981 Japan ................... 568/869

Primary Examiner—Wilbur Bascomb, Jr.

[57] ABSTRACT

Glycerine cannot be easily separated from mannitol, lactose or lactitol by atmospheric or reduced pressure distillation because of their high boiling points. Glycerine can be readily separated from mannitol, lactose or lactitol by azeotropic distillation. Typical effective agents are biphenyl, benzyl benzoate and dimethyl phthalate.

3 Claims, No Drawings

RECOVERY OF GLYCERINE FROM MANNITOL, LACTOSE OR LACTITOL BY AZEOTROPIC DISTILLATION

FIELD OF THE INVENTION

This invention relates to a method for separating glycerine from mannitol, lactose or lactitol using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

In the hydrocracking of mannitol, the molecule is broken into fragments of lower molecular weight to form compounds which belong to the glycol or polyol family. The catalytic hydrocracking of mannitol gave a mixture having the composition shown in Table 1.

TABLE 1

Polyols Produced By Hydrocracking Of Mannitol

| Compound | Weight Percent | Boiling Point, °C. |
|---|---|---|
| 2,3-Butanediol | 3.5 | 182 |
| Propylene glycol | 16.5 | 187 |
| 1,2-Butanediol | 2.0 | 192 |
| Ethylene glycol | 25.2 | 198 |
| 1,3-Butanediol | 2.7 | 206 |
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerine | 38.8 | 290 |

The highest boiling major constituent is glycerine which has a boiling point of 290° C. Table 1 lists the polyols that result from the hydrocracking of mannitol. Mannitol, lactose or lactitol do not boil even at reduced pressure. The hydrocracking reaction does not go to completion; there is always some unreacted mannitol, lactose or lactitol remaining. After the lower boiling polyols have been removed, the glycerine and the unreacted mannitol, lactose or lactitol remain. The boiling point of glycerine is so high that it will not distill off even at reduced pressure. Lactitol is also called D-glucitol, 4-O-beta-D-galactopyranosyl.

Azeotropic distillation would be an attractive method of separation of the glycerine from the mannitol, lactose or lactitol if agents can be found which will form a boiling temperature low enough to remove the glycerine without decomposing the mannitol, lactose or lactitol. Azeotropic agents would be especially attractive if (1) they formed an azeotrope containing a large amount of glycerine and (2) formed a two phase liquid mixture upon condensation. This would permit the recovery and recycle by simple decantation.

Azeotropic distillation typically requires from one to five parts as much agent as the glycerine being boiled up in the column which increases that heat requirement as well as larger diameter plates to accommodate the increased liquid and vapor in the column.

OBJECTIVE OF THE INVENTION

The objective of this invention is to provide a process or method of azeotropic distillation that will enhance the relative volatility of glycerine from mannitol, lactose or lactitol in a distillation column. It is a further object of this invention to identify organic compounds which in addition to the above constraints, are stable, can be separated from glycerine and can be recycled to the azeotropic distillation and reused with little decomposition.

SUMMARY OF THE INVENTION

The objects of this invention are provided by a process for separating glycerine from mannitol, lactose or lactitol which entails the use of certain organic compounds in an azeotropic distillation process.

DETAILED DESCRIPTION OF THE INVENTION

Table 2 lists the compounds which I have found to be effective azeotrope forming agents in the removal of glycerine from manitol, lactose or lactitol. They are 1-methyl naphthalene, biphenyl, isobornyl acetate, benzyl benzoate, dimethyl phthalate and ethyl salicylate. All except isobornyl acetate form a two phase liquid layer with glycerine and are readity separated from glycerine by decantation.

TABLE 2

Effective Agents For Separating Glycerine From Mannitol, Lactose Or Lactitol By Azeotropic Distillation

| Agent | Normal B.P., °C. | Azeo. B.P. @ 2 mm, °C. | Azeo. Comp. Wt. % Glycerine | Azeo. Phase |
|---|---|---|---|---|
| 1-Methyl naphthalene | 245 | 99 | 8 | 2 |
| Biphenyl | 255 | 115 | 25 | 2 |
| Isobornyl acetate | 228 | 109 | 10 | 1 |
| Benzyl bezote | 324 | 150 | 30 | 2 |
| Dimethyl phthalate | 283 - | 146 | 33 | 2 |
| Ethyl salicylate | 234 | 100 | 10 | 2 |

THE USEFULNESS OF THE INVENTION

The usefulness or utility of this invention can be demonstrated by referring the data presented in Table 2. The six agents listed there will separate glycerine from mannitol, lactose or lactitol at moderate temperatures and are readily separated from glycerine and ready for recycle after the separation from mannitol, lactose or lactitol.

WORKING EXAMPLES

EXAMPLE 1

Twenty-five grams of mannitol, 25 grams of glycerine and 25 grams of benzyl benzoate were placed in a distilling flask and boiled at 2 mm Hg pressure. Upon heating to 156° C., the azeotrope containing 30% glycerine and 70% benzyl benzoate boiled off. Upon condensing, the azeotropic mixture formed a two phase liquid layer. The glycerine was separated from the benzyl benzoate by decantation. The glycerine-free mannitol remained in the distilling flask.

EXAMPLE 2

Twenty-five grams of D-lactose, 25 grams of glycerine and 25 grams of dimethyl phthalate were placed in the distilling flask and boiled at 2 mm Hg pressure. Upon heating to 145° C., the azetrope containing 31% glycerine and 69% dimethyl phthalate boiled off. Upon condensing, the azeotropic mixture formed a two phase liquid layer. The glycerine was separated from the dimethyl phthalate by decantation. The glycerine-free D-lactose remained in the distilling flask.

EXAMPLE 3

Forty grams of lactitol, 23 grams of glycerine and 48 grams of dimethyl phthalate were placed in the distilling flask and boiled at 2 mm Hg pressure. Upon heating to 145° C., the azeotrope containing 31% glycerine and 69% dimethyl phthalate boiled off. Upon condensing, the azeotropic mixture formed a two phase liquid layer. The glycerine was separated from the dimethyl phthalate by decantation. The glycerine-free lactitol remained in the distilling flask.

I claim:

1. A method for recovering glycerine from a mixture of glycerine and mannitol which comprises distilling a mixture of glycerine and mannitol in a distilling column in the presence of an azeotrope forming agent, recovering the glycerine and the azeotrope forming agent as overhead product, separating the glycerine from the azetrope forming agent and obtaining the mannitol from the stillpot, wherein said azeotrope forming agent comprises one material selected from group consisting of 1-methyl naphthalene, biphenyl, isobornyl acetate, benzyl benzoate, dimethyl phthalate and ethyl salicylate.

2. A method for recovering glycerine from a mixture of glycerine and lactose which comprises distilling a mixture of glycerine and lactose in a distilling column in the presence of an azeotrope forming agent, recovering the glycerine and the azeotrope forming agent as overhead product, separating the glycerine from the azeotrope forming agent and obtaining the lactose from the stillpot, wherein said azeotrope forming agent comprises one material selected from group consisting of 1-methyl naphthalene, biphenyl, isobornyl acetate, benzyl benzoate, dimethyl phthalate and ethyl salicylate.

3. A method for recovering glycerine from a mixture of glycerine and lactitol which comprises distilling a mixture of glycerine and lactitol in a distilling column in the presence of an azeotrope forming agent, recovering the glycerine and the azeotrope forming agent as overhead product, separating the glycerine from the azeotrope forming agent and obtaining the lactitol from the stillpot, wherein said azeotrope forming agent comprises one material selected from the group consisting of 1-methyl naphthalene, biphenyl, isobornyl acetate, benzyl benzoate, dimethyl phthalate and ethyl salicylate.

* * * * *